US00PP37692P2

(12) United States Plant Patent
Barends

(10) Patent No.: US PP37,692 P2
(45) Date of Patent: Sep. 15, 2026

(54) ***SENECIO* PLANT NAMED 'Dopermanplumagpur'**

(50) Latin Name: ***Senecio* x *hybrida***
Varietal Denomination: Dopermanplumagpur

(71) Applicant: DUMMEN GROUP B.V., De Lier (NL)

(72) Inventor: Eveline Barends, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/398,512

(22) Filed: Nov. 24, 2025

(51) Int. Cl.
*A01H 5/02* (2018.01)
*A01H 6/14* (2018.01)

(52) U.S. Cl.
USPC ..... Plt./480

(58) Field of Classification Search
USPC ..... Plt./263.1, 480
See application file for complete search history.

(56) References Cited

U.S. PATENT DOCUMENTS

PP21,353 P2 * 9/2010 Miyazaki ..... A01H 6/00 Plt./480

* cited by examiner

*Primary Examiner* — Karen M Redden
(74) *Attorney, Agent, or Firm* — C. Anne Whealy

(57) ABSTRACT

A new and distinct cultivar of *Senecio* plant named 'Dopermanplumagpur', characterized by its compact, broadly upright and uniformly mounded plant habit; freely branching growth habit; dark green-colored leaves; freely flowering habit; and medium-sized daisy-type inflorescences with dark violet and dark reddish purple bi-colored ray florets.

1 Drawing Sheet

Botanical designation: *Senecio* x *hybrida*.
Cultivar denomination: 'DOPERMANPLUMAGPUR'.

CROSS-REFERENCED TO CLOSELY-RELATED APPLICATION

A European Community Plant Breeder's Rights application for the instant plant was filed by the Applicant/Assignee, Dümmen Group B.V. of De Lier, The Netherlands on Oct. 21, 2024, application number 2024/2452 and published on Dec. 15, 2024. Foreign priority is not claimed to this application.

BACKGROUND OF THE INVENTION

The present invention relates to a new and distinct cultivar of *Senecio* plant, botanically known as *Senecio* x *hybrida* and hereinafter referred to by the name 'Dopermanplumagpur'.

The new *Senecio* plant is a product of a planned breeding program conducted by the Inventor in De Lier, The Netherlands. The objective of the breeding program is to create new sturdy and freely-branching *Senecio* plants with dark green-colored leaves and numerous inflorescences with uniquely-colored ray and disc florets.

The new *Senecio* plant originated from a cross-pollination made by the Inventor in February, 2019 in De Lier, The Netherlands of a proprietary selection of *Senecio* x *hybrida* identified as code number SN-0312, not patented, as the female, or seed, parent with a proprietary selection of *Senecio* x *hybrida* identified as code number SN17-041075-004, not patented, as the male, or pollen, parent. The new *Senecio* plant was discovered and selected by the Inventor as a single flowering plant from within the progeny of the stated cross-pollination in a controlled greenhouse environment in De Lier, The Netherlands in February, 2020.

Asexual reproduction of the new *Senecio* plant by vegetative terminal cuttings in a controlled greenhouse environment in De Lier, The Netherlands since March, 2020 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dopermanplumagpur'. These characteristics in combination distinguish 'Dopermanplumagpur' as a new and distinct *Senecio* plant:

1. Compact, broadly upright and uniformly mounded plant habit.
2. Freely branching growth habit.
3. Dark green-colored leaves.
4. Freely flowering habit.
5. Medium-sized daisy-type inflorescences with dark violet and dark reddish purple bi-colored ray florets.

Plants of the new *Senecio* differ from plants of the female parent selection primarily in ray floret color as ray florets of plants of the new *Senecio* are dark violet and dark reddish purple bi-colored whereas ray florets of plants of the female parent selection are lilac and blue bi-colored.

Plants of the new *Senecio* differ from plants of the male parent selection primarily in ray floret color as ray florets of plants of the new *Senecio* are dark violet and dark reddish purple bi-colored whereas ray florets of plants of the male parent selection are mostly medium blue in color with lilac-colored bases. In addition, ray florets of plants of the new *Senecio* are longer and narrower than ray florets of plants of the male parent selection.

Plants of the new *Senecio* can be compared to plants of *Senecio hybrida* 'Sunsenepiba', disclosed in U.S. Plant Pat. No. 21,353. In side-by-side comparisons, plants of the new *Senecio* differ from plants of 'Sunsenepiba' in the following characteristics:

1. Leaves of plants of the new *Senecio* are darker green in color than leaves of plants of 'Sunsenepiba'.
2. Ray florets of plants of the new *Senecio* are dark violet and dark reddish purple bi-colored whereas ray florets of plants of 'Sunsenepiba' are purple violet and white bi-colored.

BRIEF DESCRIPTION OF THE PHOTOGRAPH

The accompanying photograph illustrates the overall appearance of the new *Senecio* plant showing the colors as true as it is reasonably possible to obtain in colored reproductions of this type. Colors in the photograph may differ slightly from the color values cited in the detailed botanical description which accurately describe the colors of the new *Senecio* plant. The photograph is a side perspective view of a typical flowering plant of 'Dopermanplumagpur' grown in a container.

DETAILED BOTANICAL DESCRIPTION

The aforementioned photograph, following observations and measurements describe plants grown during the spring in 12-cm containers in a glass-covered greenhouse in De Lier, The Netherlands and under cultural practices typically used in commercial *Senecio* production. During the production of the plants, day temperatures ranged from 8° C. to 18° C. and night temperatures ranged from 6° C. to 16° C. Plants were 13 weeks old when the photograph was taken and were 17 weeks old when the description was taken. In the following description, color references are made to The Royal Horticultural Society Colour Chart, 2007 Edition, except where general terms of ordinary dictionary significance are used.

Botanical classification: *Senecio* x *hybrida* 'Dopermanplumagpur'.

Parentage:

*Female, or seed, parent*.—Proprietary selection of *Senecio* x *hybrida* identified as code number SN-0312, not patented.

*Male, or pollen, parent*.—Proprietary selection of *Senecio* x *hybrida* identified as code number SN17-041075-004, not patented.

Propagation:

*Type*.—Terminal vegetative cuttings.

*Time to initiate roots, summer*.—About eight days at temperatures about 22° C. to 25° C.

*Time to initiate roots, winter*.—About ten days at temperatures about 18° C. to 20° C.

*Time to produce a rooted young plant, summer*.—About three weeks at temperatures about 22° C. to 25° C.

*Time to produce a rooted young plant, winter*.—About three weeks at temperatures about 18° C. to 20° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Not freely branching; medium density.

Plant description:

*Plant form and growth habit*.—Compact, broadly upright and uniformly mounded plant habit; daisy-type inflorescences positioned above the foliar plane; freely branching habit with about numerous lateral branches developing per plant; dense and bushy appearance; moderately vigorous growth habit and moderate growth rate.

*Plant height, soil level to top of foliar plane*.—About 16 cm to 20 cm.

*Plant height, soil level to top of floral plane*.—About 28 cm to 34 cm.

*Plant diameter*.—About 35 cm to 45 cm.

*Lateral branches*.—Length: About 14 cm to 19 cm. Diameter: About 5 cm to 5.5 cm. Internode length: About 4 cm to 5 cm. Strength: Moderately strong. Aspect: Mostly upright. Texture and luster: Pubescent; semi-glossy. Color, developing and developed: Close to N187A.

*Leaf description*.—Arrangement: Alternate, simple. Length: About 8 cm to 10 cm. Width: About 10 cm to 12 cm. Shape: Deltoid to rhomboidal. Apex: Acuminate. Base: Truncate. Margin: Incised; sinuses medium in depth and divergent. Texture and luster, upper surface: Sparsely pubescent, velvety; semi-glossy. Texture and luster, lower surface: Pubescent, velvety; semi-glossy. Venation pattern: Palmate. Color: Developing leaves, upper surface: Close to 137C. Developing leaves, lower surface: Close to 191D. Fully expanded leaves, upper surface: Close to N137A; venation, close to 143D. Fully expanded leaves, lower surface: Close to 194B; venation, close to between 182C and N187D. Petioles: Length: About 6 cm to 10 cm. Diameter: About 4 mm to 5 mm. Strength: Moderately strong, flexible. Texture and luster, upper and lower surfaces: Pubescent; matte. Color, upper surface: Close to N77A to N77C. Color, lower surface: Close to N199A and 200B.

Inflorescence description:

*Appearance*.—Medium-sized daisy-type inflorescences with ligulate- shaped ray florets; inflorescences arising from upper leaf axils and positioned above the foliar plane; disc and ray florets developing acropetally on a capitulum; inflorescences face mostly upright to slightly outwardly; freely flowering habit with about 220 inflorescences developing per plant during the flowering season.

*Fragrance*.—Moderately fragrant; spicy.

*Natural flowering season*.—In The Netherlands, plants of the new *Senecio* flower continuously during the spring; plants begin flowering about six to eight weeks after planting depending on temperature.

*Inflorescence longevity*.—Inflorescences last about three to five days on the plant depending on temperature; inflorescences not persistent.

*Inflorescence buds*.—Height: About 4 mm to 5 mm. Diameter: About 3 mm to 5 mm. Shape: Ovoid. Texture and luster: Rough; matte. Color: Close to 138A.

*Inflorescence size*.—Diameter: About 5 cm to 7 cm. Depth (height): About 1 cm to 2 cm. Disc diameter: About 1.2 cm to 1.5 cm.

*Receptacles*.—Height: About 4 mm to 4.5 mm. Diameter: About 6 mm to 7 mm. Shape: Rounded. Color: Close to 194A.

*Ray florets*.—Quantity and arrangement: About 12 to 14 per inflorescence arranged in a single whorl. Length: About 2 cm to 2.5 cm. Width: About 4 mm to 6 mm. Shape: Ligulate. Apex: Emarginate. Base: Obtuse. Margin: Entire; not undulate. Aspect: Initially upright to close to horizontal, flat. Texture and luster, upper surface: Smooth, glabrous; velvety; matte. Texture and luster, lower surface: Smooth, glabrous; glossy. Color: When opening, upper surface: Distally, close to N89A; proximally, close to N78A. When opening, lower surface: Close to N82A. Fully opened, upper surface: Distally, close to N88A; proximally, close to N78A; venation, close to N88A; color does not change with subsequent development. Fully opened, lower surface: Close to N87A; venation, close to N87A; color becoming closer to N88A with subsequent development.

*Disc florets*.—Quantity and arrangement: About 100 to 120 per inflorescence arranged in about eight to ten whorls. Length: About 2 mm to 4 mm. Diameter: About 0.2 mm to 0.4 mm. Shape: Ovoid; apex obtuse. Texture and luster, inner and outer surfaces: Smooth, glabrous; matte. Color: When opening, inner and outer surfaces: Close to 83A. Fully opened, inner surface: Close to 83A to 83B; venation, close to 83A; color does not change with subsequent development. Fully opened, outer surface: Close to 83A; venation, close to 83A; color does not change with subsequent development.

*Phyllaries*.—Quantity and arrangement: About 13 per inflorescence arranged in a single whorl. Length: About 6 mm to 7 mm. Width: About 1.3 mm to 1.5 mm. Shape: Lanceolate. Apex: Acute. Base: Obtuse. Margin: Entire. Texture and luster, upper and lower surfaces: Smooth, glabrous; matte. Color, upper surface: Close to 138A. Color, lower surface: Close to 138C.

*Peduncles*.—Length, terminal peduncle: About 5 cm to 7 cm. Length, third peduncle: About 3 cm to 4 cm. Diameter, terminal peduncle: About 1 mm to 1.2 mm. Diameter, third peduncle: About 1 mm. Strength: Strong. Aspect: Mostly upright. Texture and luster: Smooth, glabrous; semi-glossy. Color: Close to between 138A and 194A.

*Reproductive organs*.—Androecium: Present on disc florets only. Stamen quantity: One per disc floret. Filament length: About 1 mm to 1.1 mm. Filament color: Close to N81A. Anther size: About 1 mm by 2 mm. Anther shape: Oval. Anther color: Close to N81A. Pollen amount: Abundant. Pollen color: Close to 15A. Gynoecium: Present on both ray and disc florets. Pistil length: About 1.5 mm. Style length: About 1.2 mm. Style color: Close to N81A. Stigma shape: Crested. Stigma diameter: Less than 1 mm. Stigma color: Close to N81A.

*Seeds and fruits*.—To date, seed and fruit development has not been observed on plants of the new *Senecio*.

Pathogen & pest resistance: To date, plants of the new *Senecio* have not been observed to be resistant to pathogens and pests common to *Senecio* plants.

Temperature tolerance: Plants of the new *Senecio* have been observed to tolerate temperatures ranging from about 2° C. to about 30° C. and to be suitable for USDA Hardiness Zones 9a to 12b.

It is claimed:

1. A new and distinct *Senecio* plant named 'Doperman-plumagpur' as herein illustrated and described.

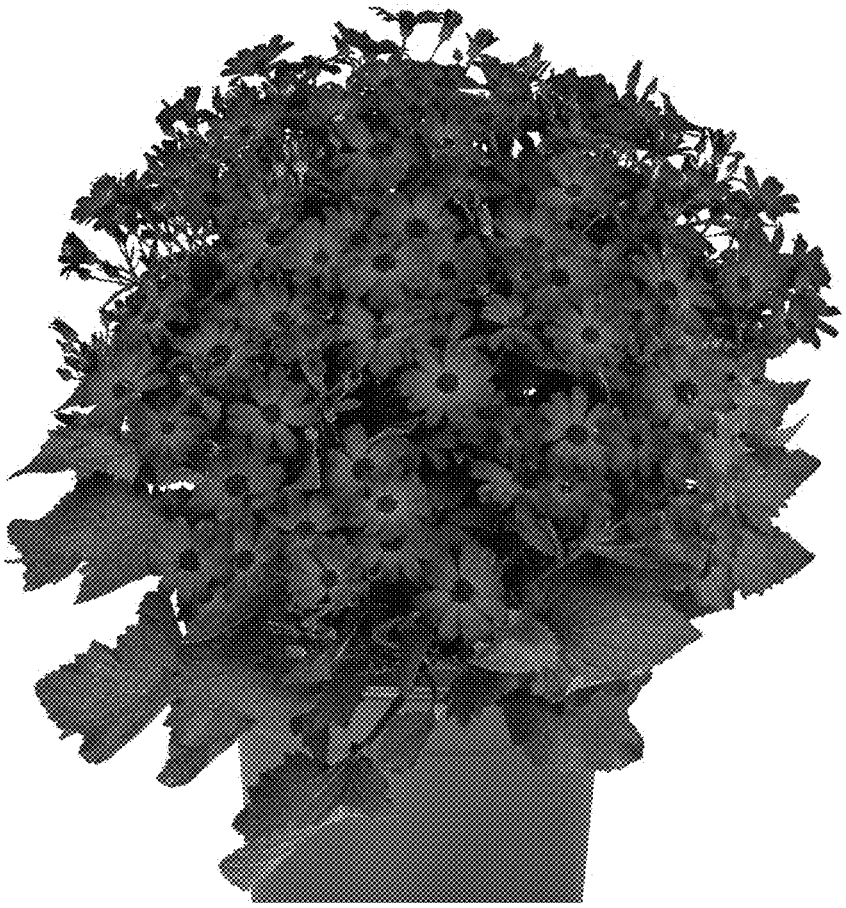

* * * * *